US00PP11193P

United States Patent [19]

Van Leuven

[11] Patent Number: Plant 11,193

[45] Date of Patent: Jan. 25, 2000

[54] APPLE TREE NAMED 'FIERO'

[75] Inventor: Myles Van Leuven, Kennewick, Wash.

[73] Assignee: Columbia & Okanagan Nursery, Wenatchee, Wash.

[21] Appl. No.: 08/962,529

[22] Filed: Oct. 31, 1997

[51] Int. Cl.[7] ..... A01H 5/00

[52] U.S. Cl. ..... Plt./168

[58] Field of Search ..... Plt./34.1, 168

[56] References Cited

U.S. PATENT DOCUMENTS

P.P. 10,141 12/1997 Auvil ..... Plt./34.1

*Primary Examiner*—Howard J. Locker
*Assistant Examiner*—Melissa L. Kimball
*Attorney, Agent, or Firm*—Klarquist Sparkman Campbell Leigh & Whinston

[57] ABSTRACT

A new and distinct variety of apple tree named 'Fiero' characterized by early maturity, maturing 10 to 14 days earlier than ('Yataka Fuji') and 30 to 40 days earlier than standard 'Fuji', and an overall pinkish red blush coloration in contrast to the predominantly striped pattern of coloration typical of ('Yataka Fuji') and standard 'Fuji'.

6 Drawing Sheets

BACKGROUND OF THE INVENTION

The present invention comprises a new and distinct variety of apple tree, referred to by the varietal name 'Fiero'.

The original tree of the new variety was discovered by me in 1992 as a whole tree mutation in a block of an early 'Fuji' ('Yataka Fuji', U.S. Plant Pat. No. 7,001) being grown in a cultivated area in Prescott, Wash. I noticed that this single tree, planted in 1991, had an earlier apple maturity than other trees in the block of the same age. Specifically, apples from trees of my new variety mature about mid-September in central Washington state. By comparison, apples from 'Yataka' trees, an early 'Fuji' strain, normally mature in late September to early October, and apples from standard 'Fuji' (not patented) trees mature in late October to early November. Apples from trees of my new variety also have a more intense blushed color than 'Yataka' apples.

The 'Fiero' variety was compared to other 'Fuji' strains, as set forth or specified below, and, particularly to the 'Yataka' variety and standard 'Fuji'. Fruit from all the compared strains were grown in Prescott, Wash. and were from trees of similar age.

This invention has not been observed under all possible environmental conditions. However, the following combination of traits have been repeatedly observed in asexually propagated progeny (asexually propagated by grafting both at Prescott, Wash., and in Wenatchee, Wash.) and are the basic characteristics of this invention that in combination distinguish this variety of apple as a new and distinct variety: (1) matures 10 to 14 days earlier (about mid-September in central Washington) than 'Yataka' and 30 to 40 days earlier than standard 'Fuji' or any of the so-called higher color mutations of standard 'Fuji', e.g., 'Nagafu 2', 'Nagafu 6', 'Nagafu 12', 'BC 1', and 'Akifu 1' (all unpatented) and of the patented strains 'TAC 114' (U.S. Plant Pat. No. 8,032) and 'Myra' (U.S. Plant Pat. No. 9,645); and (2) an overall pinkish red blush coloration in contrast to the predominantly striped pattern of coloration typical of 'Yataka' and standard 'Fuji'.

Asexual reproduction shows that these characteristics are established and transmitted through succeeding asexual propagations.

BRIEF DESCRIPTION OF THE DRAWINGS

The following photographs illustrate typical characteristics of the new variety as noted, with color being as true as is reasonably possible to make the same in this type of color photograph.

DETAILED DESCRIPTION

Figure 1:
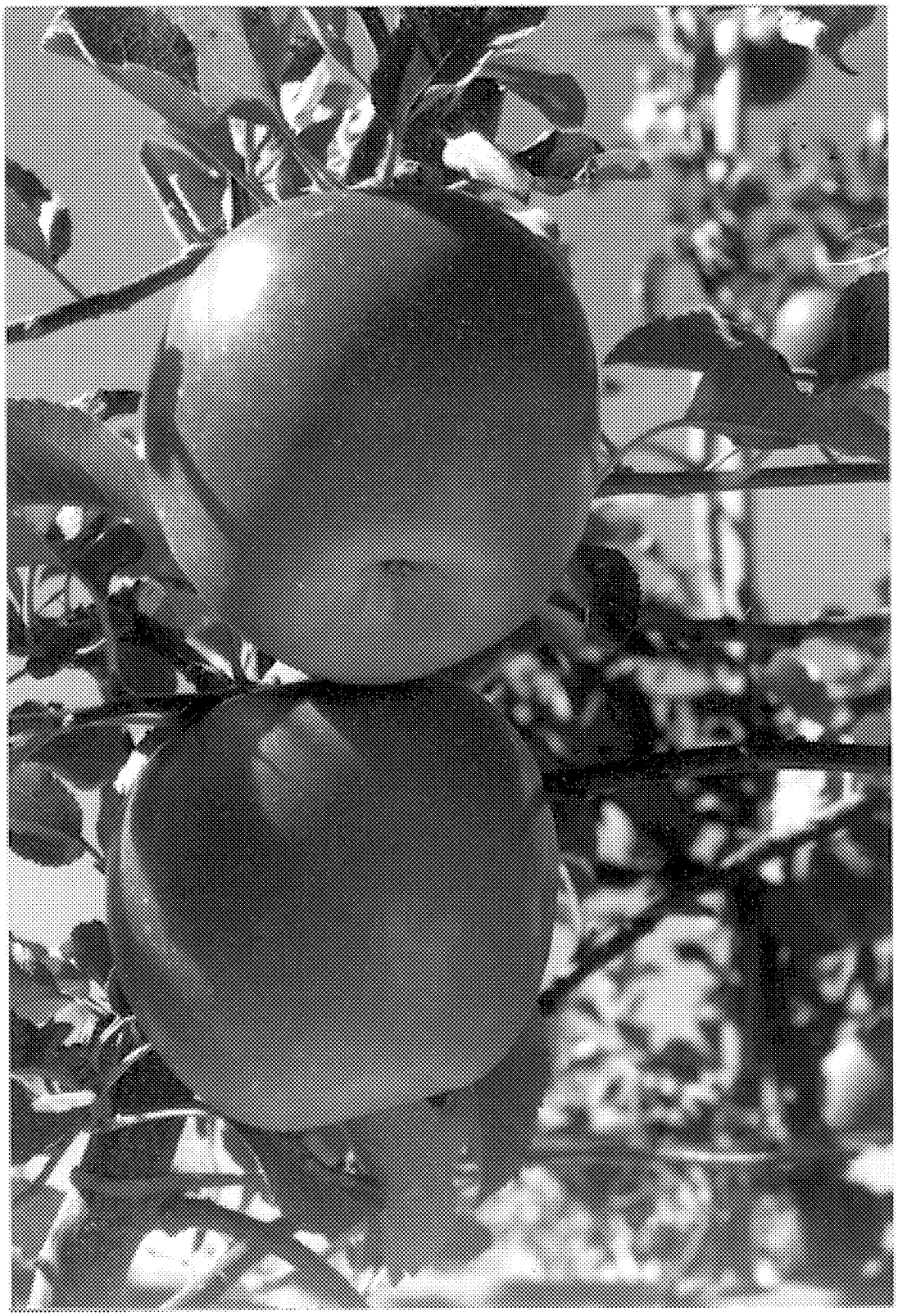
FIG. 1 is a view of typical fruit of 'Fiero' on a tree.
Figure 2:
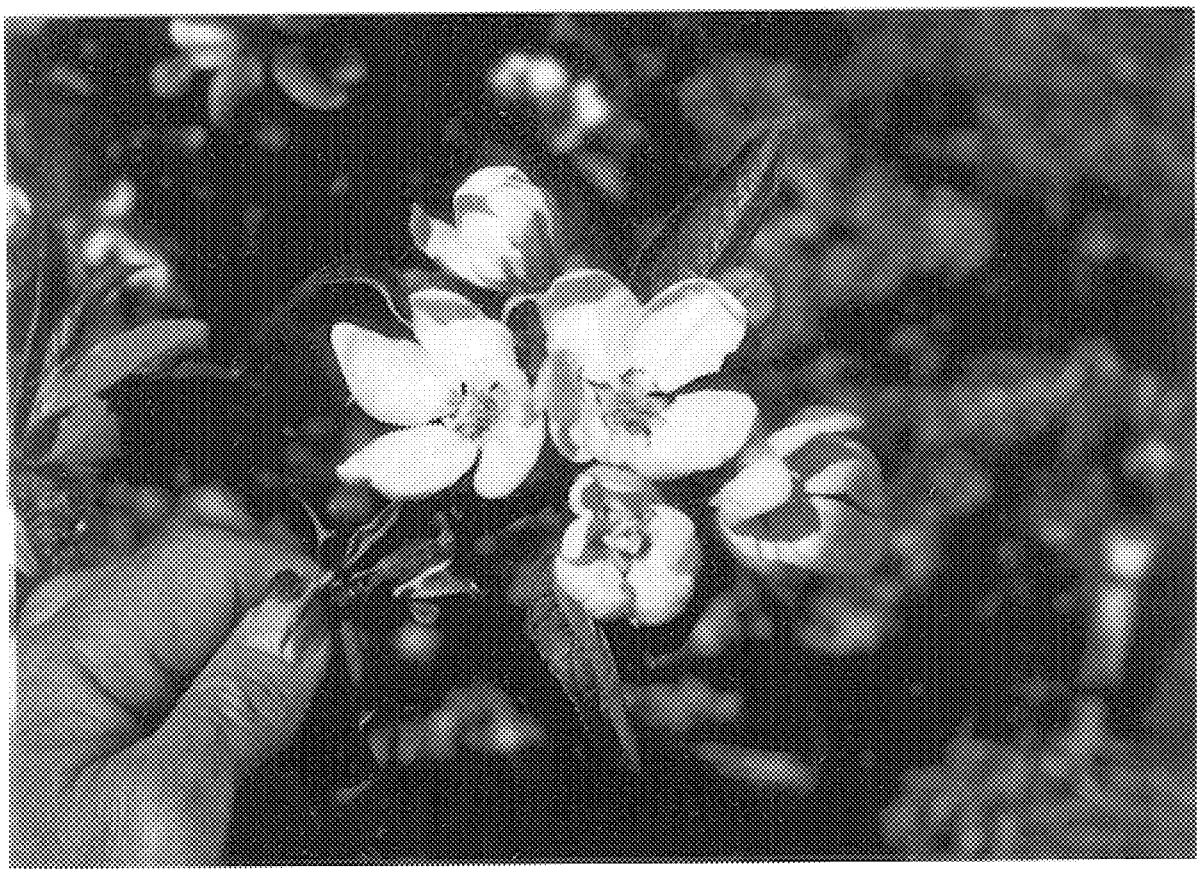
FIG. 2 is a close-up view of flowers of 'Fiero'.
Figure 3:
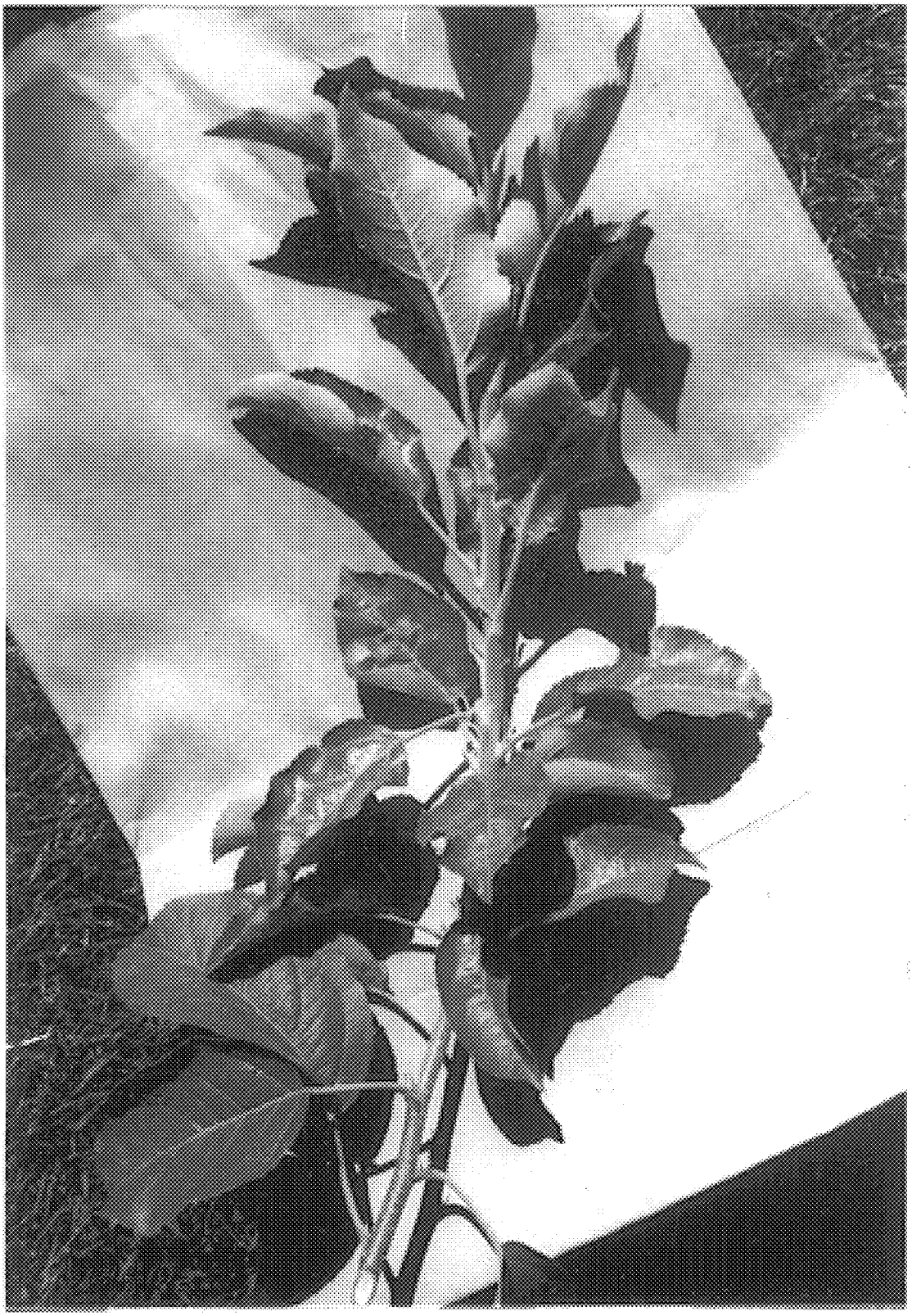
FIG. 3 is a view of vegetative shoots of 'Fiero'.

The following is a detailed description of the invention based on plants produced under orchard practices at Broetje Orchards, Prescott, Wash., and observed at this location from 1992 to 1997. Plants were also produced and observed at C&O Nurseries, Wenatchee, Wash.

Color references are made in accordance with the Munsell Limited Color Cascade, except where general color terms of ordinary dictionary significance is obvious.

All trees of the new variety, insofar as I have been able to observe them, have been identical in all the characteristics described below. All measurements are an average of 10 typical samples.

Species: *Malus pumila* Mill.

Parentage: Whole tree mutation of 'Yataka Fuji'.

Propagation: Holds to distinguishing characteristics through succeeding propagation by grafting.

Locality where grown and observed: Prescott, Wash., and Wenatchee, Wash.

Dates of first and last picking: September 13 to 26.

Trees:

*Size.*—Medium. Vigor similar to, but less than, standard 'Fuji'.

*Habit.*—Somewhat spreading.

*Trunk.*—Stocky, smooth, gray-green to light brown (Munsell Color 7.5 YR 4/2).

*Branches.*—Spreading, wide angles.

*Dormant one-year-old shoot.*—Medium thickness (8.3 mm), reddish brown to light brown (Munsell Color 10 RP 3/2), lenticels cream colored, elongated, medium in density and size, about 1 mm.

*Internodes.*—Average internodes length on one-year-old shoot medium (32 mm).

Leaves: Broad, dark green, medium glossy on upper surface, finely pubescent on lower surface.

*Size.*—Broad. Length 70–105 mm, average 87 mm. Width 47–55 mm, average 52 mm.

*Color.*—Upper surface, dark green (Munsell Color 10 GY 2/4 10 to GY 3/4); lower surface, medium green (Munsell Color 10 GY 4/4 10 to GY 5/4).

*Margin.*—Serrate.

*Tip.*—Sharply pointed.

*Petiole.*—Medium, 20–25 mm, medium thick, 1.7–1.9 mm, finely pubescent, yellow green (Munsell Color 5 GY 6/6).

*Stipules.*—Insignificant, in pairs, pointed 5 mm in length.

Flower: Identical to 'Yataka Fuji'. First bloom midseason, just before or after Apr. 20, 1997, in Prescott, Wash. Full bloom approximately Apr. 27, 1997.

*Size.*—Medium-large, about 50 mm.

*Color.*—Purplish pink when unopened, white when opened.

*Petals, position of margins.*—Touching to overlapping.

*Stamen.*—Single row, anthers bright yellow.

*Pistil.*—Stigma medium length, flat at top, rounded at base; styles medium, fused at base.

*Sepals.*—Medium size, pubescent.

*Pollination requirements.*—Compatible with all cultivars, except 'Fuji' and its sports, that bloom in the same time period.

Fruit: Maturity when described was mid-harvest period (mid-September); firmness 18–20 pounds; soluble solids 14–16%; starch index (1–6 scale) 3.0–3.5. Size: Medium to large, 83.6 mm to 74.4 mm (280–350 grams).

*Form.*—Round to occasionally oblong, usually symmetric, length/diameter ratio approximately 1:1, with ribbing absent, a slight crowning at the distal (calyx) end, with lobes either absent or inconspicuous.

*Cavity.*—Broad, medium depth (15 mm).

*Basin.*—Medium to deep (11–14 mm), wide (30–35 mm), slightly pubescent.

*Stem.*—Medium length (26 mm), medium thickness (2.2 mm).

*Calyx.*—Medium size, lobes convergent from base toward center, finely pubescent, calyx closed.

*Locules (carpels).*—Medium to small, closed.

Skin: Smooth, without bloom, lacking greasiness. Medium thickness, with no tendency toward cracking. Russeting generally absent, but similar to standard 'Fuji', which can show occasional russet caused by environment or caustic sprays. Russet, where found, was on exposed cheek or around the base.

*Ground color.*—Yellow-green (Munsell Color 5 Y 8/10).

*Lenticels.*—Medium in size and density, overall effect inconspicuous. Color: White to light tan.

*Overcolor.*—Pinkish to red blush (Munsell Color 5 R 4/10), with indistinct striping prior to autumn maturity. Range of overcolor 60–100%, depending upon exposure.

*General color effect.*—Higher red color at comparable maturity than either early 'Fuji' clones or standard 'Fuji', and more like the unpatented red 'Fuji' strains, 'BC-2', 'Nagafu 2', and 'Nagafu 12'.

*Flesh.*—Yellowish white in color, very juicy, sweet (14.0 to 16.0 Brix), acidity low (approximately 0.4% malic acid); firmness at harvest 18 pounds, somewhat coarse, nonastringent and mild in flavor. General dessert quality is excellent, very similar to other 'Fuji' strains.

*Core.*—Round shape, small to medium size. Seed cells closed.

*Seeds.* —8–12 fully developed seeds, obovate shape, medium size, adhering strongly to the carpel wall. Length: 7 mm. Breadth: 4 mm.

*Color.*—Brown.

*Use.*—Fresh eating, dessert.

*Storage.*—Keeping quality is maintained for up to 8 months in CA, 4 to 5 months in common storage at 32° F. (0° C.).

*Productivity.*—Production to date has been identical to that of adjacent 'Fuji' trees. Fruit is borne predominantly on spurs and terminally on short shoots. Some tendency toward alternate bearing, similar to standard 'Fuji', but easily controllable by proper thinning.

Resistance to pests and disease, hardiness: No apparent difference from standard 'Fuji' in susceptibility to insects and diseases. No evidence of winter damage or frost damage different from standard 'Fuji'.

Figure 5:
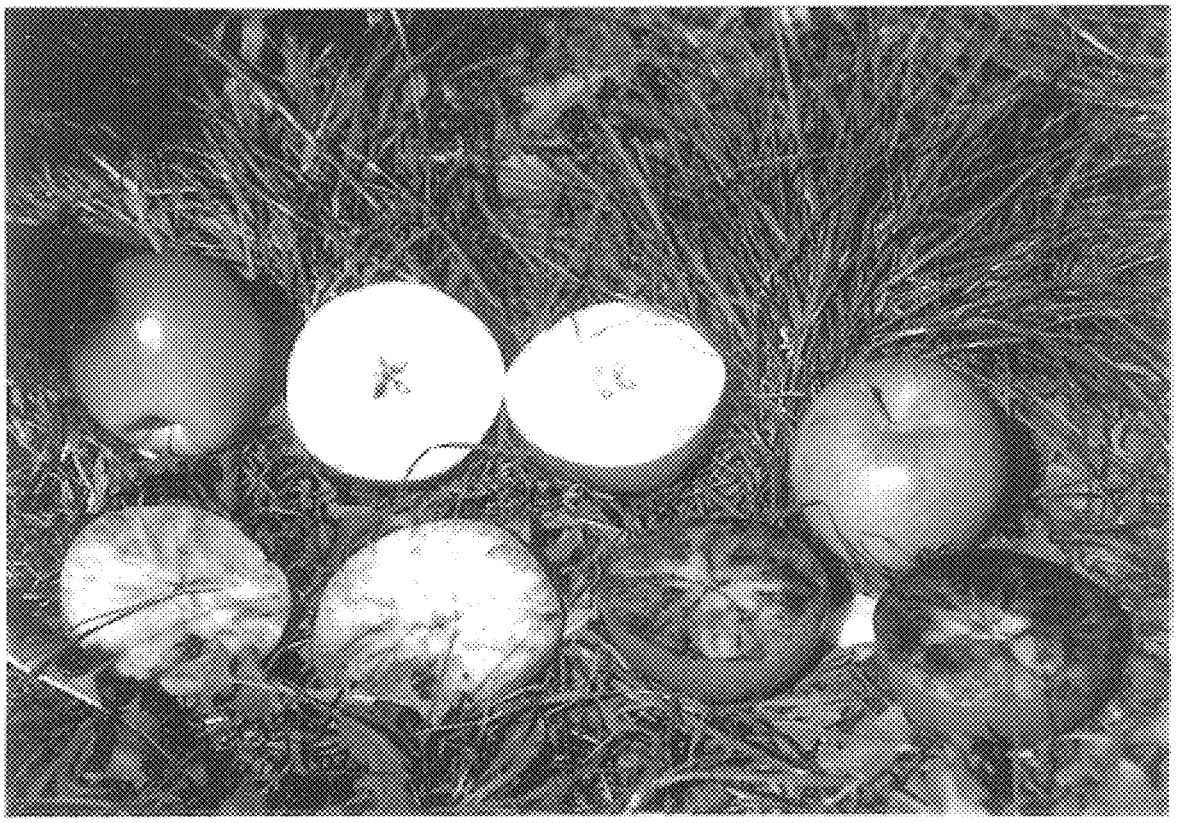
FIG. 5 is a comparison of the degree of starch conversion in fruits of 'Fiero' and 'BC 2' (not patented). The upper row includes (from left to right) a whole 'Fiero' fruit, a transversely sectioned 'Fiero' fruit, a transversely sectioned 'BC 2' fruit, and a whole 'BC 2' fruit. The lower row includes (from left to right) two halves of a 'Fiero' fruit and two halves of a 'BC 2' fruit, each of which is stained with iodine. Photograph taken Sep. 13, 1995.
Figure 6:
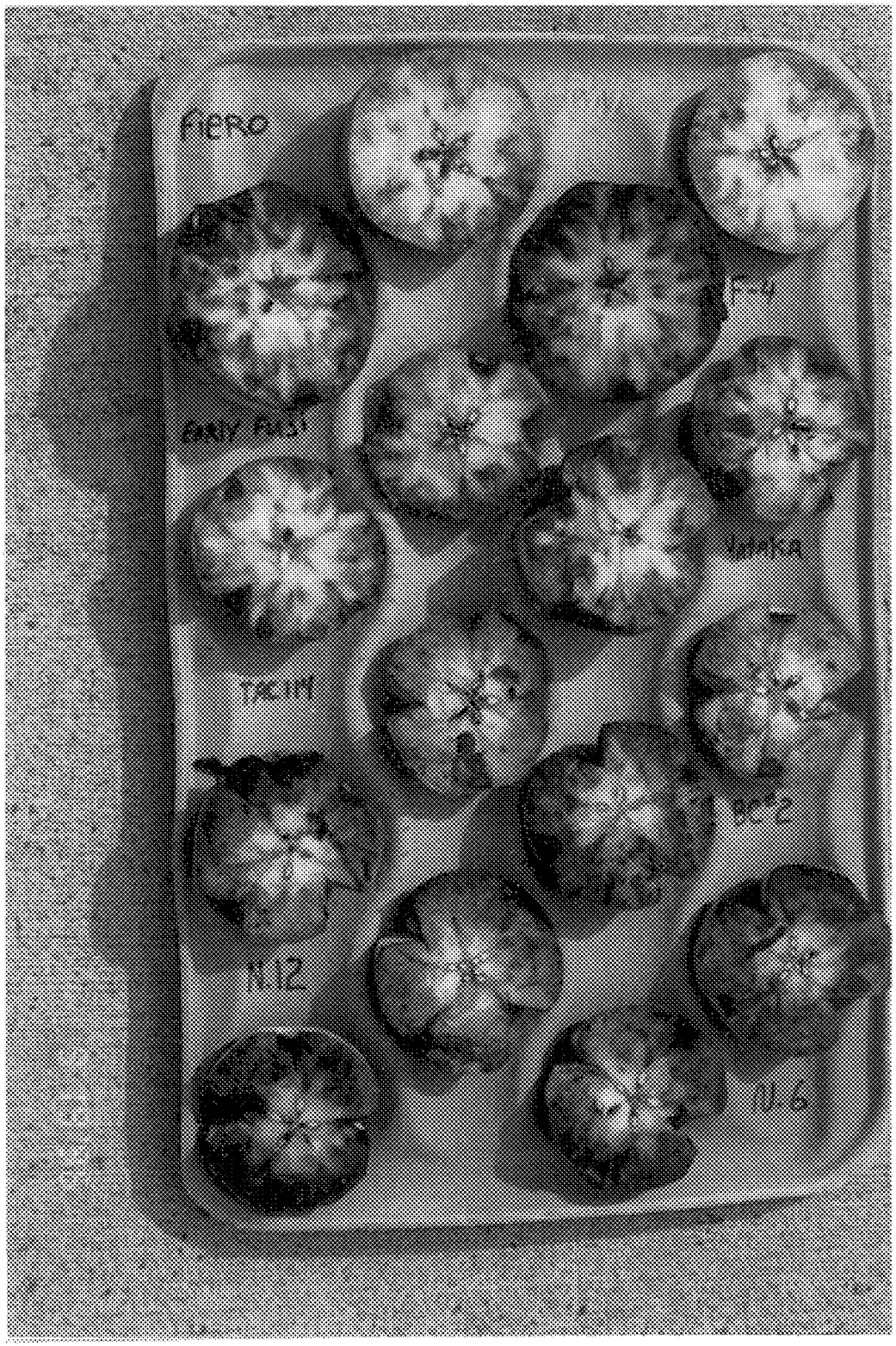
FIG. 6 depicts eight horizontal rows of iodine-stained fruit, each row containing two halves of a fruit from the variety identified in the row to compare the degree of starch conversion in fruit of the following 'Fuji' clones: 'Fiero'; F-4 selection; early 'Fuji' selection; 'Yataka'; 'TAC 114'; 'BC-2'; 'Nagafu 12'; and 'Nagafu 6' (of these strains, only 'Yataka' (U.S. Plant Pat. No. 7,001) and 'TAC 114' (U.S. Plant Pat. No. 8,032) are patented). The FIG. 6 photograph was taken Sep. 19, 1996, and shows that much more of the starch has been converted in 'Fiero' fruit in the top row than in the fruit of the other varieties.

The earlier maturity date of fruit of my new 'Fiero' variety is demonstrated by the greater starch conversion of my new variety in comparison to that of other varieties. In FIGS. 5 and 6, sectioned fruit are stained with iodine, which stains starch a purplish-black. Darker fruits have more starch and thus a lower degree of maturity. Fruits of 'Fiero' display significantly lighter staining that the other varieties tested, demonstrating their earlier maturity.

The early maturity date of my new variety is also apparent from the average harvest date. In particular, in Prescott, Wash., average harvest dates have been observed as follows:

| Strain | Ave. Harvest Date |
|---|---|
| Fiero | September 13–20 |
| Early Fuji F-4 strain | September 18–25 |
| Early Fuji ('Yataka fuji') | September 23–27 |
| TAC 114 (PP 8,032) | October 13–20 |
| Myra (PP 9,645) | October 10–22 |
| BC 2 | October 18–25 |
| Nagafu 12 | October 18–25 |
| Nagafu 6 | October 20–30 |

Figure 4:
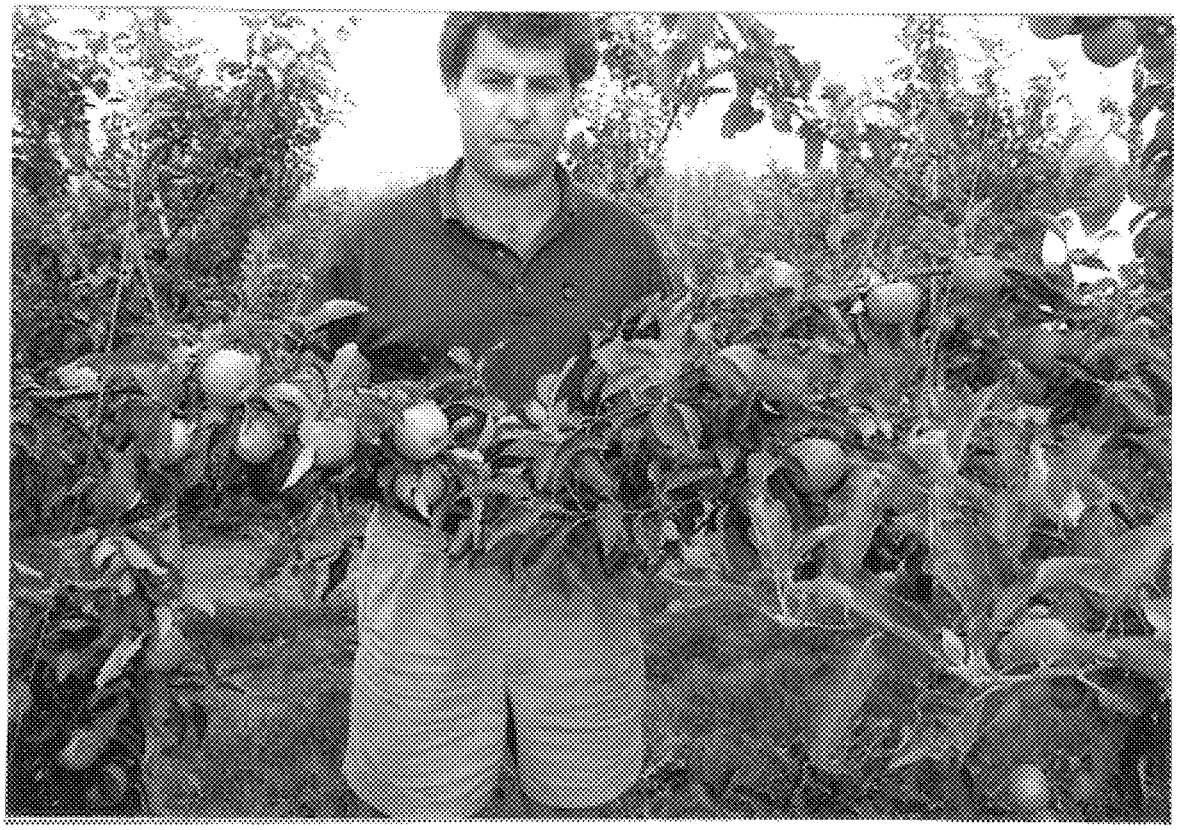
FIG. 4 is a comparison of fruit-bearing branches of 'Fiero' and 'BC 2'.

Fruit of my new variety have an overall pinkish red blush over a substantial percentage of the surface area in combination with the early maturity. This is apparent from FIG. 4, showing 'BC 2' fruit and 'Fiero' fruit on a side by side comparison and also from the following table:

| Strain | Color Pattern | Amount |
|---|---|---|
| Fiero | Pink–red blush | 60–100% |
| Early Fuji F-4 strain | Red blush | 60% |
| Early Fuji ('Yataka fuji') | Red stripe | 30–50% |
| TAC 114 | Red stripe + blush | 50–80% |
| Myra | Pink blush and stripe | 50–80% |
| BC 2 | Mostly red blush | 60–90% |
| Nagafu 12 | Light stripe + blush | 60–90% |
| Nagafu 6 | Striped, some blush | 50–70% |

My 'Fiero' variety thus represents a new and highly desirable new 'Fuji' cultivar.

I claim:

1. A new and distinct variety of apple tree as herein shown and described.

* * * * *